United States Patent [19]

Hoelderich et al.

[11] Patent Number: 4,772,746
[45] Date of Patent: Sep. 20, 1988

[54] PREPARATION OF 4-PENTENOATES

[75] Inventors: Wolfgang Hoelderich, Frankenthal; Rolf Fischer, Heidelberg; Klaus-Dieter Malsch, Schifferstadt; Hubert Lendle, Ludwigshafen, all of Fed. Rep. of Germany

[73] Assignee: BASF Aktiengesellschaft, Ludwigshafen, Fed. Rep. of Germany

[21] Appl. No.: 870,108

[22] Filed: Jun. 3, 1986

[30] Foreign Application Priority Data

Jun. 14, 1985 [DE] Fed. Rep. of Germany ....... 3521380

[51] Int. Cl.$^4$ .......................................... C07C 67/333
[52] U.S. Cl. .................................................. 560/205
[58] Field of Search ......................... 560/205; 585/666

[56] References Cited

U.S. PATENT DOCUMENTS 3,475,511 10/1969 Manning .............................. 585/666
4,332,966 6/1982 Isogai et al. .......................... 560/206
4,529,815 7/1985 Schneider et al. ................... 560/205

OTHER PUBLICATIONS

Bull. of the Chem. Soc. of Japan, Band 46, Seite 528.

Primary Examiner—Michael L. Shippen
Attorney, Agent, or Firm—Keil & Weinkauf

[57] ABSTRACT

4-Pentenoates are prepared by isomerization by a process in which isomeric pentenoates are treated at elevated temperatures in the presence of a zeolite containing metals of group eight of the Periodic Table and the 4-pentenoate is distilled off from the reaction mixture, and the zeolite contains iron, cobalt and/or nickel.

7 Claims, No Drawings

PREPARATION OF 4-PENTENOATES

In the preparation of pentenoates by reacting butadiene with carbon monoxide and an alkanol in the presence of a metal carbonyl catalyst, as described in, for example, German Laid-Open Application No. 3,040,432, a mixture of isomeric pentenoates is obtained. However, for further reactions, for example for the preparation of δ-formylvalerates by hydroformylation of pentenoates, 4-pentenoates are preferred starting compounds. Attempts have therefore been made to obtain 4-pentenoates by isomerization of isomeric pentenoates. However, Bull. Chem. Soc. Japan, 46, 528 dicloses that the isomerization of methyl 3-pentenoate in the presence of a cobalt carbonyl gives predominantly methyl 2-pentenoate. In another procedure described in Tetrahedron 28 (1972), 5769–5777, it is possible, in the presence of a complex of rhodium-triphenylphosphine and tin chloride, to shift the equilibrium in the isomerization so that 4-pentenoates are obtained. However, the catalyst used in this procedure is deactivated in the course of a few hours.

EP-A No. 126,349 describes a process for the preparation of 4-pentenoates from a mixture of pentenoates by treatment with an acidic zeolite which contains noble metals of group eight of the Periodic Table.

In the isomerization Of the pentenoate, five isomers, i.e. the 4-pentenoate, the cis- and trans-3-pentenoates and the cis- and trans-2-pentenoates, are present when thermodynamic equilibrium is reached, the equilibrium being shifted strongly toward the trans-2-pentenoate.

It is an object of the present invention to provide a process for the preparation of 4-pentenoates from isomeric pentenoates, in which the catalyst used retains its activity over a fairly long time, the linear displacement of the double bond to give the 4-pentenoate takes place preferentially and furthermore the cis-2-pentenoate, which is difficult to separate off, is formed in a very small amount.

We have found that this object is achieved by a process for the preparation of 4-pentenoates by isomerization, in which isomeric pentenoates are treated in the presence of a zeolite containing metals of Group eight of the Periodic Table at elevated temperatures and the 4-pentenoate is distilled off from the reaction mixture, wherein the zeolite contains iron, cobalt and/or nickel.

The novel process has the advantages that the catalysts used have a long life and are cheaply available and that the double bond preferentially undergoes a linear displacement to give the 4-pentenoate. A particular advantage of the novel process is that the formation of the cis-2-pentenoate, which is difficult to separate off, is minimized or even completely suppressed. The reaction mixture obtained is easier to separate by distillation.

Advantageously used starting materials are isomeric pentenoates, for example 2- or 3-pentenoates, which are derived from alcohols of not more than 12 carbon atoms. Isomeric alkyl pentenoates, in particular pentenoates of alcohols of not more than 4 carbon atoms, are particularly preferably used. Examples of suitable starting materials are methyl 3-pentenoate, ethyl 3-pentenoate, propyl 3-pentenoate, butyl 3-pentenoate, methyl 2-pentenoate, ethyl 2-pentenoate and propyl 2-pentenoate. Mixtures of isomeric pentenoates, as obtained in the reaction of butadiene with carbon monoxide and alcohols in the presence of metal carbonyls as described in German Laid-Open Application DOS No. 3,040,432, are also useful. 3-Pentenoates have become particularly important.

Zeolites are crystalline aluminosilicates which possess a highly ordered structure comprising a rigid three-dimensional network of $SiO_4$ and $AlO_4$ tetrahedra which are bonded by common oxygen atoms. The ratio of silicon and aluminum atoms to oxygen is 1:2. The electrovalency of the aluminum-containing tetrahedra is compensated by inclusion of cations in the crystal, for example alkali metal ions or hydrogen ions. Cation exchange is possible. Prior to dehydration by drying or calcination, the voids between the tetrahedra are occupied by water molecules.

Zeolites are divided into different groups, depending on their structure (cf. Ullmanns Encyclopädie der technischen Chemie, 4th edition, volume 24, page 575, (1983). For example, members of the mordenite group contain chains, and those of the chabasite group layers, of tetrahedra having the zeolite structure, whereas in the faujasite group the tetrahedra are arranged to form polyhedra, for example a cubooctahedron, which is composed of four-membered and six-membered rings. Preferred zeolites are A, X and Y zeolites, particularly the last-mentioned ones.

The zeolites are isolated, dried, as a rule at from 100° to 160° C., preferably 110° C. and calcined at from 450° to 550° C., preferably 500° C. They are advantageously converted to extrudates or tablets together with a binder in a weight ratio of from 90:10 to 40:60. Examples of suitable binders are alumina, preferably boehmite, finely divided alumina, amorphous aluminosilicates having a ratio of $SiO_2$ to $Al_2O_3$ of from 25:75 to 90:5, in particular 75:25, silica, in particular finely divided silica, mixtures of finely divided silica and finely divided alumina, finely divided titanium dioxide, and clay. After the molding procedure, the extrudates or tablets are dried at from 100° to 160° C. for from 2 to 24 hours and then calcined at from 450° to 550° C. for from 2 to 24 hours.

Advantageous catalysts are also obtained if the zeolite isolated is molded directly after drying, and is calcined only after the molding procedure. The zeolites prepared can, however, also be used in pure form, without a binder, as extrudates or tablets. In this case, molding is carried out with the addition of extrusion assistants or peptization agents, such as hexamethylcellulose, stearic acid, potato starch, formic acid, acetic acid, oxalic acid, nitric acid, ammonia, amines, silicoesters, graphite or mixtures of these.

If, because of the method of preparation, the zeolite is not in the preferred acidic H form but in, for example, the sodium form, the latter can advantageously be converted completely or partially to the H form by ion exchange with ammonium ions followed by calcination, or by treatment with an acid.

The zeolites used contain iron, cobalt and/or nickel, the content of the stated metals advantageously being from 0.1 to 7.0% by weight based on the zeolite. It has proven particularly useful for the zeolites to contain cobalt. It has also proven advantageous if, in addition to the abovementioned metals of group eight, the catalysts used also contain alkali metal ions, such as sodium ions or potassium ions, in particular sodium ions, or alkaline earth metal ions, such as calcium ions or barium ions, in particular calcium ions. The content of alkali metal and/or alkaline earth metal ions is advantageously from 0.05 to 3.5% by weight, based on the zeolite.

Doping is advantageously effected by a method in which, for example, the molded zeolite is initially taken in a riser tube, and an aqueous and/or amine-containing solution of a halide or nitrate of the metals described is passed over at from 20° to 100° C. Ion exchange of this type can be carried out, for example, on the hydrogen, ammonium or alkali metal form of the zeolite. Another possible method of applying the metal to the zeolite is to impregnate the latter with a halide, a nitrate or an oxide of the metals described above, in an aqueous and/or alcoholic and/or amine-containing solution. Both ion exchange and impregnation are followed by one or more drying processes and, if desired, repeated calcination.

In one possible embodiment, for example, $Co(NO_3)_2$ .6 $H_2O$ is dissolved in water, and this solution is used to impregnate the molded or unmolded zeolite, as a rule for from 1 to 30 minutes. Excess water is distilled off, and the impregnated zeolite is then dried at from 100° to 160° C. and calcined at from 450° to 550° C. This impregnation process can be repeated several times in succession until the desired metal content is reached.

It is also possible to suspend pure zeolite powder in an aqueous solution of cobalt nitrate at from 40° to 500° C. for a period of, for example, up to 24 hours, while stirring. The product is filtered off and is dried and calcined at the temperatures stated above, after which the zeolite material obtained in this manner can be further processed with or without a binder to give extrudates or pellets.

The zeolites present in the H form, the ammonium form or the sodium form can be subjected to ion exchange, for example as follows: the zeolite which has been molded with or without a binder and is in the form of extrudates or pellets is initially taken in a column, and an aqueous Solution of cobalt nitrate is circulated over the said zeolite at from 30° to 80° C. for from 15 to 20 hours. The zeolite is then washed thoroughly with water and is dried and calcined at the abovementioned temperatures.

In the case of zeolites which are doped with the abovementioned metals of group eight of the Periodic Table, an after-treatment with hydrogen, for example at from 200° to 500° C., has proven advantageous. Before the treatment with hydrogen, the catalyst is advantageously slowly heated at not more than 350° C. in the presence of molecular oxygen or of a gas containing this. It is also advantageous if the hydrogen used contains olefins with 2 to 4 carbon atoms.

In another possible method of modification, the molded or unmolded zeolite is treated with an acid, such as hydrochloric acid, hydrofluoric acid or phosphoric acid, and/or with steam. By precoking, it is also possible to adjust the activity of the catalyst to achieve optimum selectivity.

The catalysts described here can be used alternatively in the form of 2–4 mm extrudates, as tablets having a diameter of from 3 to 5 mm or in the form of a powder having a particle size of from 0.1 to 0.5 mm.

During isomerization, the temperature is generally maintained at from 50° to 300° C. The isomerization is generally carried out under atmospheric pressure but, depending on the type of ester used, reduced pressure or superatmospheric pressure, e.g. up to 50 bar, may also be employed.

The isomerization may be carried out batchwise by suspending the catalyst powder in the isomer mixture, for example in a stirred container, and heating the mixture for from 2 to 20 hours at from 50° to 250° C., in particular 100° to 200° C.

The isomerization is preferably carried out continuously. To do this, a reaction tube is filled with the molded catalyst, and the mixture of isomeric pentenoates is pumped in liquid form through the tube at from 50° to 250° C., in particular from 100° to 200° C., preferably from 100° to 120° C., the mean residence time being from 5 to 100 minutes. The 4-pentenoate is separated off from the resulting mixture by distillation, and the remaining mixture is recycled.

The isomerization is particularly preferably carried out in the gas phase. In this case, the vaporized mixture of isomeric pentenoates is passed over the catalyst, for example in the form of a fluidized bed, in the presence or absence of an inert carrier gas, such as nitrogen. A temperature of from 150° to 300° C., in particular from 160° to 250° C., is advantageously maintained. It has proven advantageous to maintain a space velocity (WHSV; grams of starting mixture per gram of catalyst per hour) of from 0.1 to 20 $h^{-1}$. As a rule, the mixture obtained in vapor form is condensed, and the 4-pentenoate is then separated off by distillation. The remaining isomers are advantageously recycled to the isomerization.

If, when the zeolite catalysts are used according to the invention, deactivation due to coking occurs, it is advisable to regenerate the zeolites by burning off the coke ceposit with air or with a mixture of air and nitrogen at from 400° to 550° C., in particular from 490° to 540° C. As a result of this, the zeolites regain their initial activity.

4-Pentenoates are useful for the preparation of δ-formyl valerates, which are intermediates for the preparation of ε-caprolactam, hexanediol or adipic acid.

The Examples which follow illustrate the process.

PREPARATION OF THE CATALYSTS

Catalyst A

Sodium Y zeolite is molded with boehmite in a weight ratio of 60:40 to give 2 mm extrudates, and the latter are dried at 110° C. and calcined at 500° C. for 16 hours. These extrudates are treated in a column with a 20% strength by weight ammonium chloride solution in a weight ratio of 1:15, at 80° C. This ion exchange is repeated until the sodium content is <0.15% by weight. The product is then dried at 110° C. and calcined at 500° C. for 5 hours. The extrudates treated in this manner are impregnated with a cobalt nitrate solution, dried repeatedly at 110° C. and calcined at 540° C. for 2 hours. The cobalt content is 3.3% by weight.

Catalyst B

Sodium Y zeolite is molded with boehmite in a weight ratio of 60:40 to give 2 mm extrudates, and the latter are dried at 110° C. and calcined at 500° C. for 16 hours. These extrudates are treated in a column with 20% by weight calcium nitrate solution in a weight ratio of 1:15, at 80° C. The product is then dried at 110° C. and calcined at 500° C. for 5 hours. The extrudates obtained in this manner are treated repeatedly in a column with a cobalt nitrate solution at 80° C. for 2 hours, after which they are dried at 130° C. and calcined at 540° C. for 2 hours. Catalyst B contains 1.2% by weight of cobalt, 0.5% by weight of sodium and 0.1% by weight of calcium.

Catalyst C (comparison)

A Y zeolite which is laden with 0.5% by weight of palladium, as described in EP-A No. 126 349, is used as the catalyst.

EXAMPLES 1 TO 3

A tube reactor having an internal diameter of 0.6 cm and a length of 90 cm is charged with the catalyst, and methyl 3-pentenoate in vapor form is passed over the catalyst at 180° C. under isothermal conditions. The gas mixture which emerges is condensed, and the composition is determined by gas chromatography. Details of the conditions and results are shown in the table below.

TABLE

|  | Examples | | Comparative Example |
|---|---|---|---|
|  | 1 | 2 | 1 |
| Catalyst | A | B | C |
| Temperature | 180° C. | 180° C. | 180° C. |
| WHSV | 2 h$^{-1}$ | 2 h$^{-1}$ | 2 h$^{-1}$ |
| Product composition, % by weight | | | |
| 4-PAE | 4.4 | 10.4 | 10.7 |
| 3-PAE | 92.6 | 81.4 | 75.3 |
| trans 2-PAE | 3.0 | 8.2 | 13.1 |
| cis 2-PAE | 0 | 0 | 0.9 |

*PAE = methyl pentenoate

Other by-products were undetectable under the reaction conditions chosen.

EXAMPLE 3

The procedure described in Example 2 is followed. After a reaction time of 6 hours, the content of 4-PAE falls to 8.1% by weight.

COMPARATIVE EXAMPLE 2

The procedure described in Comparative Example 1 is followed. After a reaction time of 6 hours, the content of 4-PAE falls to 6.78% by weight.

We claim:

1. A process for the preparation of a 4-pentenoate by isomerization which comprises:

heating a mixture of 3-pentenoates in a reactor to a temperature of from 50° to 300° C. in the presence of a zeolite catalyst containing from 0.1 to 7.0% by weight of iron, cobalt and/or nickel, and distilling off from the reaction mixture the 4-pentenoate that is formed.

2. The process of claim 1, wherein the zeolite contains cobalt.

3. The process of claim 1, wherein the zeolite additionally contains alkali metal and/or alkaline earth metal ions.

4. The process of claim 1, wherein the zeolite contains from 0.05 to 3.5% by weight of alkali metal and/or alkaline earth metal ions.

5. The process of claim 1, wherein the isomerization is carried out in the gas phase at from 100° to 200° C.

6. The process of claim 1, wherein the 4-pentenoate is 4-methylpentenoate.

7. The process of claim 6, wherein the zeolite is a Y zeolite.

* * * * *